United States Patent
Maeda et al.

(10) Patent No.: US 7,781,409 B2
(45) Date of Patent: Aug. 24, 2010

(54) COMPOSITION FOR EXTERNAL USE

(75) Inventors: Mitsuru Maeda, Shiga (JP); Masahiro Nakao, Kyoto (JP); Harukazu Fukami, Kyoto (JP)

(73) Assignee: Suntory Holdings Limited, Osaka (JP)

( * ) Notice: Subject to any disclaimer, the term of this patent is extended or adjusted under 35 U.S.C. 154(b) by 631 days.

(21) Appl. No.: 10/561,916

(22) PCT Filed: Jun. 25, 2004

(86) PCT No.: PCT/JP2004/009012

§ 371 (c)(1), (2), (4) Date: Mar. 23, 2007

(87) PCT Pub. No.: WO2005/000319

PCT Pub. Date: Jan. 6, 2005

(65) Prior Publication Data

US 2007/0269454 A1    Nov. 22, 2007

(30) Foreign Application Priority Data

Jun. 26, 2003    (JP) .............................. 2003-183610

(51) Int. Cl.
*A61K 31/047*    (2006.01)
*A61K 36/00*    (2006.01)
*C12N 1/00*    (2006.01)

(52) U.S. Cl. .......................... 514/25; 514/23; 424/725; 435/254.3; 435/913; 435/914; 435/918

(58) Field of Classification Search .................. None
See application file for complete search history.

(56) References Cited

U.S. PATENT DOCUMENTS

2002/0031574 A1 *  3/2002  Takeda et al. .................. 426/11
2005/0048128 A1    3/2005  Miyata et al.

FOREIGN PATENT DOCUMENTS

| JP | 53-98954 | | 8/1978 |
| JP | 05013647 | * | 4/1993 |
| JP | 05103647 A | * | 4/1993 |
| JP | 06263790 | * | 9/1993 |

(Continued)

OTHER PUBLICATIONS

Egawa et al., "Whitening effect of vitamin C and its derivatives," Fragrance Journal, 1997, vol. 25, No. 9, pp. 28-36.

(Continued)

*Primary Examiner*—Patricia Leith
(74) *Attorney, Agent, or Firm*—Drinker Biddle & Reath LLP

(57) ABSTRACT

A composition for external use, comprising 2-O-(β-D-glucopyranosyl)ascorbic acid represented by the formula (I):

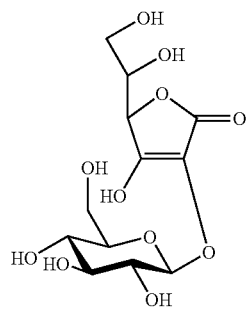

or a salt or ester thereof which is safe to the human body, and a koji mold or a processed koji. The composition for external use is excellent in skin permeability, containing an ascorbic acid derivative which is excellent in stability, utilized persistently in the living body, and strong in antioxidant activity, and has little skin irritation.

9 Claims, 3 Drawing Sheets

FOREIGN PATENT DOCUMENTS

| | | |
|---|---|---|
| JP | 7-274977 | 10/1995 |
| JP | 10-234356 A | 9/1998 |
| JP | 2000-169339 | 6/2000 |
| JP | 2003-041414 A | 2/2003 |
| JP | 2003-055149 A | 2/2003 |
| JP | 2003-55244 | 2/2003 |
| JP | 2003-171290 | 6/2003 |
| WO | WO 02/55047 A1 | 12/2001 |
| WO | WO 03/057707 A1 | 7/2003 |

OTHER PUBLICATIONS

Supplementary European Search Report in Application No. EP 04746481.3 mailed Feb. 25, 2009.

* cited by examiner

COMPOSITION FOR EXTERNAL USE

TECHNICAL FIELD

The present invention relates to a skin external preparation, more particularly, to a skin external preparation such as cosmetics, quasi-drugs and the like having excellent whitening effect on the skin such as prevention of occurrence of pigmentation after sunburn.

BACKGROUND ART

For the purpose of imparting prescribed medical efficacy, drug efficacy ingredients are added to a skin external preparation such as medicaments, quasi-drugs (e.g. ointments), and cosmetics (e.g. milky lotions, creams, lotions, packs, gels, foundations).

For example, in order to prevent melanism of the skin generated by sunburn, and phenomena such as spot, freckle and the like generated by excessive pigmentation of a melanin pigment, whitening ingredients such as calamine, L-ascorbic acids, hydroquinone glycosides, cinnamic aldehyde, and a placenta extract are added.

Among them, ascorbic acids are an extremely excellent whitening factor which is highly safe, promotes collagen synthesis, scavenges active oxygen, suppresses shortening of a telomere gene, and induces a skin tissue, and are widely utilized in medicaments, cosmetics, foods, feeds and the like. On the other hand, since normal derivatives of L-ascorbic acid are easily oxidatively degraded, and are unstable when formulated into preparations, those derivatives cannot be put into practice as they are. For the purpose of stabilizing them, a composition containing at least one kind of ascorbic acid derivatives or salts thereof in an aqueous alkali ion (JP-A-2000-351905), L-ascorbate-2-phosphate (JP-A-2000-143485), and α-glycosyl-L-ascorbic acid (JP-A-2002-53450, JP-A-2002-121115) have been proposed. However, actions and effects of them are not necessarily satisfactory.

That is, although stabilization was secured, particularly, there was a problem that only salts of these ascorbic acids and derivatives thereof result in poor absorbability.

In addition, a method of facilitating permeation of ascorbic acid derivatives into the skin by iontophoresis (ion introducing instrument) designed for permeation of an ionic substance into a deep portion of the skin by electric repulsion, cavitation suppression-type sonophoresis (ultrasound introducing instrument), or IPL (strobe visible light) has been adopted, but there was a problem that special instruments are required therefor.

On the other hand, as a transdermal absorption promoter to be contained in a composition for external use, dimethyl sulfoxide, dimethylacetamide, methyldecyl sulfoxide and the like disclosed in U.S. Pat. No. 3,551,554, a combination with lower alkylamide (e.g. combination of dimethylacetamide with ethyl alcohol, isopropyl alcohol or isopropyl palmitate) disclosed in U.S. Pat. No. 3,472,431, and a combination of 2-pyrrolidone with a suitable oily substance, for example, an ester of straight aliphatic acid and an alcohol of 2 to 6 carbon atoms disclosed in U.S. Pat. No. 4,017,641. However, there is a possibility that these known transdermal absorption promoters have all skin irritation, causing redness or edema on the skin.

DISCLOSURE OF THE INVENTION

An object of the present invention is to provide a skin composition for external use excellent in skin permeability, containing an ascorbic acid derivative which is excellent in stability, utilized persistently in the living body, and strong in antioxidant activity, and has little skin irritation.

The present inventors extensively studied the aforementioned problems of the prior art and, as a result, succeeded in creating 2-O-(β-D-glucopyranosyl)ascorbic acid which is a novel compound, a salt thereof, and an ester thereof (hereinafter, also abbreviated as ascorbic acid derivative of the present invention), and found out that these are excellent in stability, utilized persistently in the living body, and strong in antioxidant activity, and have little skin irritation. Further, the present inventors found out that the ascorbic acid derivative of the present invention is useful as a skin external preparation such as cosmetics and quasi-drugs. Moreover, in the case where the ascorbic acid derivative of the present invention is used as a skin external preparation, the present inventors have extensively studied in order to improve permeability of the ascorbic acid derivative of the present invention to the skin and, as a result, have found out an unexpected new finding that when the ascorbic acid derivative of the present invention is used by combining with a koji mold or a processed koji, skin permeability of the ascorbic acid derivative of the present invention is remarkably improved. That is, it was found that a koji mold or a processed koji promotes skin permeability of the present ascorbic acid. Originally, a skin consists of about 0.01 mm outermost corneum, about 0.1 mm epidermis inner thereto, and about 0.1 to 1.3 mm dermis inner thereto and, even when ascorbic acid or an ascorbic acid derivative is applied to the skin, permeability into the skin tissue is not necessarily better. However, when a combination of the ascorbic acid derivative of the present invention and a koji mold or a processed koji is applied to the skin surface, the ascorbic acid derivative of the present invention is rapidly absorbed until the dermis layer, where it is gradually degraded to vitamin C, vitamin C is released over a long period of time, and its bioavailability is high. In addition, the present inventors studied activity of a novel compound 2-O-(β-D-glucopyranosyl)ascorbic acid of the present invention and, as a result, found out that the compound is extremely useful as provitamin C, such as improvement in stability, and persistent utilization in the living body as compared with 2-O-(α-D-glucopyranosyl)ascorbic acid.

That is, the present invention relates to:

(1) a composition for external use, comprising 2-O-(β-D-glucopyranosyl)ascorbic acid represented by the formula (I):

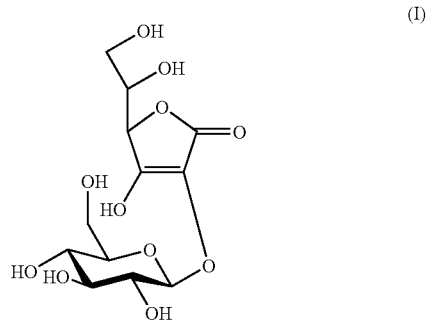

or a salt or ester thereof which is safe to the human body, and a koji mold or a processed koji, (2) the composition according to the above (1), which is a cosmetic or a quasi-drug, (3) the composition according to the above (1) or (2), wherein the 2-O-(β-D-glucopyranosyl)ascorbic acid represented by the formula (I) as defined in the above (1) is 2-O-(β-D-glucopyranosyl)ascorbic acid extracted from a plant, (4) the composition according to the above (3), wherein the plant is a plant of Solanaceae, (5) the composition according to the above (3) or (4), wherein the plant is Chinese wolfberry, or its raw fruit or dry fruit, (6) the composition according to any one of the above (1) to (5), wherein the koji mold is a mold belonging to the genus *Aspergillus*, (7) the composition according to any one of the above (1) to (6), wherein the koji mold is a mold belonging to *Aspergillus oryzae*, *Aspergillus kawachii* or *Aspergillus awamori*, (8) a set of a composition comprising 2-O-(β-D-glucopyranosyl)ascorbic acid represented by the formula (I) as defined in the above (1), or a salt or ester thereof which is safe to the human body, and a composition comprising a koji mold or a processed koji, (9) a composition comprising 2-O-(β-D-glucopyranosyl) ascorbic acid, or a salt or ester thereof which is safe to the human body, for the set as defined in the above (8), and

(10) an agent for potentiating skin permeability of 2-O-(β-D-glucopyranosyl)ascorbic acid, or a salt or ester thereof which is safe to the human body, comprising a koji mold or a processed koji.

According to the present invention, a skin composition for external use excellent in skin permeability, and containing an ascorbic acid derivative which is excellent in stability, utilized persistently in the living body, and strong in antioxidant activity, and has little skin irritation can be provided.

BEST MODE FOR CARRYING OUT THE INVENTION

Figure 1:
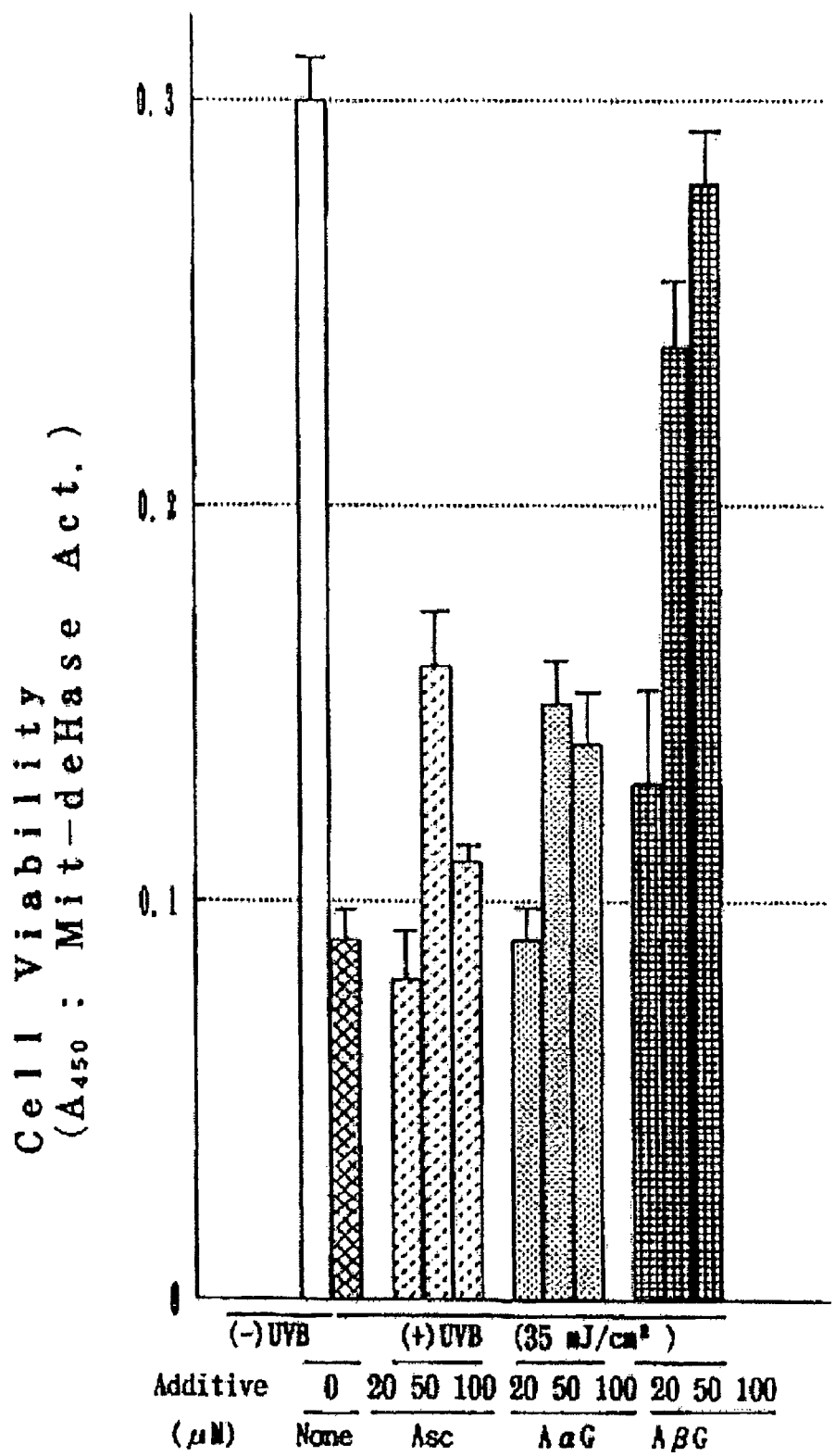
FIG. 1 shows a protective effect of 2-O-(β-D-glucopyranosyl)ascorbic acid on cell death of keratinocytes (HaCaT) derived from the human skin epidemis due to ultraviolet-ray B wave (UVB) irradiation.

Examples of producing 2-O-(β-D-glucopyranosyl)ascorbic acid used in the present invention include a method of extraction from a plant or a treated plant, and a production method by a chemical synthesis or enzyme method. The method of extraction from a plant is performed by extraction from a Solanaceae plant or a treated Solanaceae plant, particularly, Chinese wolfberry, or a raw fruit or dry fruit of Chinese wolfberry. A preferable process for producing the ascorbic acid derivative of the present invention and a composition containing the same will be exemplified below.

A synthetic intermediate of the present 2-O-(β-D-glucopyranosyl)ascorbic acid is 2-O-(2,3,4,6-tetra-O-acetyl-β-D-glucopyranosyl)ascorbic acid. 2-O-(2,3,4,6-tetra-O-acetyl-β-D-glucopyranosyl)ascorbic acid which is an intermediate can be synthesized as follows. That is, the hydroxy group at the position 3 of commercially available 5,6-O-isopropylidene ascorbic acid is subjected to selective benzyletherification to obtain 3-O-benzyl-5,6-O-isopropylidene ascorbic acid by the known method described in J. Med. Chem., 31, 793, 1988. This 3-O-benzyl compound as an aglycon can be converted into β-glycoside by a conventional glucosylation reaction, thereby to obtain 2-O-(2,3,4,6-tetra-O-acetyl-β-D-glucopyranosyl)-3-O-benzyl-5,6-O-isopropylidene ascorbic acid. For example, it can be obtained by heating (2,3,4,6-tetra-O-acetyl-(3-D-glucopyranosyl)carbonic acid ester (Kei Komura, Tokyo Institute of Technology, doctoral thesis, 1977) together with the 3-O-benzyl compound at 100 to 200° C. in a non-polar solvent, or without a solvent. As the carbonic acid ester, alkyl, halogenated alkyl, or optionally substituted aryl carbonic acid ester can be used. Alternatively, it can be also obtained by using a (2,3,4,6-tetra-O-acetyl-(β-D-glucopyranosyl) halide, adding a dehydrating agent, and performing the reaction in the presence of a mercury salt or a silver salt in a solvent of halogenated hydrocarbon such as chloroform and methylene chloride, or a solvent of aromatic hydrocarbon such as benzene and toluene (Lodd's Chemistry of Carbon Compounds IF, 320, 1967, Elsvier).

The isopropylidene group of 2-O-(2,3,4,6-tetra-O-acetyl-β-D-glucopyranosyl)-3-O-benzyl-5,6-O-isopropylidene ascorbic acid can be removed by hydrolysis with an acid catalyst. For example, heating is performed at 40 to 100° C. in 30% to 80% aqueous acetic acid solution. Alternatively, heating is performed at room temperature to a reflux temperature in the presence of p-toluenesulfonic acid in acetone or methyl ethyl ketone. Further, the reaction can be performed similarly while adding water to the reaction system.

The benzyl group of 2-O-(2,3,4,6-tetra-O-acetyl-β-D-glucopyranosyl)-3-O-benzyl ascorbic acid can be removed by conventional hydrogenolysis. For example, debenzylation can be performed using palladium carbon or palladium black, or platinum carbon or platinum black as a catalyst in the presence of hydrogen in a protonic polar solvent such as acetic acid and an alcohol, or a non-polar solvent such as benzene, toluene and ethyl acetate.

These steps of such deprotection may be performed in a reverse order. That is, after 2-O-(2,3,4,6-tetra-O-acetyl-(β-D-glucopyranosyl)-3-O-benzyl-5,6-O-isopropylidene ascorbic acid is debenzylated, the resulting 2-O-(2,3,4,6-tetra-O-acetyl-β-D-glucopyranosyl)-5,6-O-isopropylidene ascorbic acid may be subjected to deprotection of isopropylidene group with an acid catalyst.

As described above, 2-O-(2,3,4,6-tetra-O-acetyl-β-D-glucopyranosyl)ascorbic acid which is the title intermediate can be obtained.

A method of chemically synthesizing 2-O-(β-D-glucopyranosyl)ascorbic acid using the aforementioned intermediate will be described.

2-O-(β-D-glucopyranosyl)ascorbic acid can be obtained by hydrolyzing the acyl group of 2-O-(2,3,4,6-tetra-O-acetyl-β-D-glucopyranosyl)ascorbic acid with an alkali. As the alkali, there can be used an aqueous solution of sodium hydroxide, potassium hydroxide or the like, an aqueous solution of carbonates such as potassium carbonate, sodium carbonate, potassium bicarbonate and sodium bicarbonate, or a metal alcoholate such as sodium methylate. In order to dissolve 2-O-(2,3,4,6-tetra-O-acetyl-(3-D-glucopyranosyl) ascorbic acid as a raw material in these solutions, a mixed solution of alcohols such as methanol and ethanol may be used. The optimum reaction temperature is 0° C. to room temperature. The reaction solution is neutralized with hydrochloric acid, sulfuric acid, a cation exchange resin or the like. In the case of hydrochloric acid or sulfuric acid, it is necessary to remove the produced salt, but in the case of a cation exchange resin, a desalting procedure is not necessary because a sodium or potassium radical is adsorbed. By freeze-drying or concentrating the neutralized reaction solution under reduced pressure, an objective compound can be obtained. In addition, depending on the purpose, the product may be purified by column chromatography.

A process for producing a 2-O-(β-D-glucopyranosyl) ascorbic acid-containing extract through extraction from Chinese wolfberry will be described.

An extract containing 2-O-(β-D-glucopyranosyl)ascorbic acid can be obtained by immersing a raw fruit or dry fruit (Lycium chinense) of Chinese wolfberry directly or in the ground state in hot water or aqueous ethanol, and concentrating under reduced pressure, freeze-drying, or spray-drying the extract obtained by solid-liquid separation. The alcohol concentration at this immersion is preferably 10% to 95%, and immersion days are preferably 3 to 7 days. The content of 2-O-(β-D-glucopyranosyl)ascorbic acid in the extract of Lycium chinense is 0.86 to 1.2%, and a composition having an enriched content can be obtained by the following method. That is, a solution obtained by dissolving the extract of Lycium chinense in distilled water, or immersing a raw material in a 5 to 50-fold amount, preferably 8 to 10-fold amount of distilled water is diluted with distilled water, and the diluted solution is passed through a strongly basic anion exchange resin such as DOWEX® 1-X8 (trade name) manufactured by Dow Chemical, and Amberlite IRA-400 (trade name) manufactured by Rohm & Haas, thereby to adsorb the substance. After sufficient washing with water, a fraction containing the substance is obtained by stepwise elution or gradient elution using acetic acid. The fraction is subjected to concentration under reduced pressure or freeze-drying treatment to remove acetic acid, thereby to obtain a composition containing about 30 to 50% 2-O-(β-D-glucopyranosyl)ascorbic acid.

A process for producing a composition containing 2-O-(β-D-glucopyranosyl)ascorbic acid by an enzyme method will be explained.

The present inventors intensively studied production of a commercially available enzyme preparation and, as a result, found that cellulase "ONOZUKA", PANCELLASE BR (Yakult Pharmaceutical Ind. Co., Ltd.), CELLULOSIN Hankyu Kyoei Bussan), cellulase (Sigma), (β-glucosidase (Toyobo Co., Ltd.), and β-glucosidase (Nakarai Tesque) enzyme preparations have β-glucosyltransferase activity. Glucosetransferase used in the present invention may be any one as far as it acts on a solution containing a compound having a β-glucosyl group, and ascorbic acid, and synthesizes 2-O-(β-D-glucopyranosyl)ascorbic acid through transglycosylation reaction, and is not limited on the origin and the kind, but a cellulase preparation derived from genus Trichoderma, and a β-glucosidase preparation derived from almond are preferable from a viewpoint of yields.

In the transferase reaction, it is desirable that concentrations of cellobiose and ascorbic acid are as high as possible, and around 0.3 M and 0.2 M are preferable. It becomes also possible to use cellobiose which is a substrate for an enzyme from a compound containing other β-glucosyl group, for example, polymeric glucan such as cellulose, carboxymethylcellulose and the like by combining with a suitable hydrolase. In addition, when each enzyme is immobilized and used as an enzyme reactor, it is possible to effectively produce 2-O-(β-D-glucopyranosyl)ascorbic acid. On the other hand, as ascorbic acid which is to be a recipient for a transfer reaction, free ascorbic acid is preferable from a viewpoint of stability during the reaction and a transfer yield, but even an ascorbic acid salt such as an alkali metal salt and an alkaline earth metal salt of ascorbic acid, or a mixture thereof can also produce 2-O-(β-D-glucopyranosyl)ascorbic acid. The present inventors also found out that a free isoascorbic acid and an isoascorbic acid salt also serve as a recipient for a transfer reaction. Therefore, ascorbic acid and an ascorbic acid derivative used in a transglycosylation reaction can be used depending on the purpose and, usually, not only free ascorbic acid, but also sodium ascorbate and calcium ascorbate can be appropriately used, if necessary.

The enzyme reaction proceeds in a range of a pH 2 to 8, and it is preferable to retain the pH at 4 to 6 in view of an optimal pH for an enzyme. As regard the reaction temperature, the reaction proceeds at 20 to 60° C., and it is desirable to retain a temperature at around 30 to 40° C. in view of stability and an optimal temperature for an enzyme. It is desirable that an addition amount of an enzyme is 20 to 400 units (one unit indicates an enzyme titer at which 1 μmol of p-nitrophenol is released per minute) per 1 g of cellobiose. The enzyme may be added at once or may be added by dividing into a few times while monitoring the reaction by high performance liquid chromatography. Alternatively, an enzyme may be immobilized on a suitable resin carrier, for example, an ion exchange resin, a hydrophobic resin or the like, and the enzyme may be used as an enzyme reactor in the reaction. The reaction time is sufficiently around 1 to 4 days, and a reaction endpoint may be determined while monitoring the reaction.

An ascorbic acid derivative produced after completion of the reaction can be separated by a conventional separating means such as membrane separation, ion exchange column chromatography, active carbon column chromatography and the like. For example, as a strongly acidic cation exchange resin, there can be appropriately used an alkali metal salt type, an alkaline earth metal salt type, or a H+type of a styrene-divinylbenzene crosslinked copolymer resin to which a sulfonic acid group is bound. Examples of a commercially available product include Dowex 50W×8 (trade name) manufactured by Dow Chemical, Amberlite CG-120 (trade name) manufactured by Rohm & Haas, and Diaion SK104 (trade name) manufactured by Mitsubishi Chemical Corporation. Thereupon, separated unreacted ascorbic acid and a compound containing a β-glucosyl group may be reused as a raw material for enzyme reaction.

Further, in order to obtain a highly purified product, the product can be purified by high performance liquid chromatography. That is, the purified product can be obtained by a combination of a saccharide/organic acid analyzing column and a volatile acid such as acetic acid and trifluoroacetic acid, or a combination of an ODS column, sublimating ammonium formate, a volatile ion pair regent for analyzing an acidic substance, and di-n-butylamine acetate. The substance was identified to be a natural substance by comparative analysis between mass spectroscopy and nuclear magnetic resonance spectrum of 2-O-(β-D-glucopyranosyl)ascorbic acid obtained by chemical synthesis.

The ascorbic acid derivative of the present invention includes not only a free acid which is 2-O-(β-D-glucopyranosyl)ascorbic acid, but also a salt or ester thereof which is safe to the human body. Examples of the salt include a sodium salt and a potassium salt, and examples of the ester include acetic acid ester and propionic acid ester. The salt or the ester is obtained by a method of reacting a free acid with a base (e.g. sodium hydroxide, potassium hydroxide) or by an acylation reaction, and these are reactions well-known to a person skilled in the art.

Then, physiological activity of the ascorbic acid derivative of the present invention will be explained.

Suppression of disorder due to ultraviolet-ray irradiation by 2-O-(β-D-glucopyranosyl)ascorbic acid Pure 2-O-(β-D-glucopyranosyl)ascorbic acid obtained by the aforementioned method or chemical synthesis clearly suppressed more strongly cell death of keratinocytes (HaCaT) derived from the human skin epidermis due to ultraviolet-ray B wave (UVB) irradiation at the same concentration as compared with ascorbic acid or 2-O-(α-D-glucopyranosyl)ascorbic acid.

It is known that when a part of the skin of a nude mouse is irradiated with light (290 to 400 nm) near a wavelength spectrum of solar light, ascorbic acid (vitamin C) among various antioxidant factors contained in the mouse skin is decreased most rapidly (Photodermatol Photoimmunol Photomed., 10 (5), 183, 1994). In addition, inducement of skin inflammation due to UVB irradiation after shaving the back of a guinea pig was suppressed by external application of ascorbic acid or 2-O-(α-D-glucopyranosyl)ascorbic acid, and 2-O-(α-D-glucopyranosyl)ascorbic acid has the higher effect (Fragrance Journal, Vol.25, No. March, pp.55, 1997). Further, it is reported that by pre-administration of a 10% aqueous ascorbic acid solution to the pig skin for consecutive days from 3 days to one week, ultraviolet-ray disorder can be alleviated (Br. J. Dermatol., 121, 247, 1992).

Therefore, it is strongly suggested that 2-O-(β-D-glucopyranosyl)ascorbic acid has the higher effect on suppression of skin inflammation due to ultraviolet-ray irradiation or other ultraviolet-ray disorder than ascorbic acid or 2-O-(a-D-glucopyroansyl)ascorbic acid.

In addition, regarding a concentration of intracellular ascorbic acid in a human skin keratinocytes, 2-O-(β-D-glucopyranosyl)ascorbic acid is maintained at a highest concentration for a longest term. Such the maintenance of intracellular ascorbic acid at a high concentration by 2-O-(β-D-glucopyranosyl) ascorbic acid acts on cells protection due to UVB irradiation. In addition, it is evident that 2-O-(β-D-glucopyranosyl)ascorbic acid serves naturally within cells as provitamin C which is converted into ascorbic acid. Prevention of wrinkle/sagging by 2-O-(β-D-glucopyranosyl)ascorbic acid Further, regarding collagen synthesis by normal human dermal fibroblasts (NHDF), 2-O-(β-D-glucopyranosyl) ascorbic acid has higher activity as compared with 2-O-(α-D-glucopyranosyl)ascorbic acid or ascorbic acid. It is thought that this is because a concentration of intracellular ascorbic acid is persistently maintained at high level. That is, it is thought that collagen synthesis promoting action of ascorbic acid occurs also in fibroblasts derived from the skin, and this serves for regeneration or reconstruction of the skin. It is reported that a burn patient was actually cured without scar by applying ascorbic acid 2-phosphate which is one of stable ascorbic acids (Japanese Cosmetic Science Society, Lecture Abstract pp.50, 1998). On the other hand, it is also known that ascorbic acid suppresses an enzyme which degrades collagen, and an enzyme which degrades elastin necessary for elasticity of the skin (Bioantioxidant Provitamin C, pp.63, 1999, Fragrance Journal). These facts demonstrate that 2-O-(β-D-glucopyranosyl)ascorbic acid has the effect of preventing wrinkle and sagging.

Whitening effect due to activity of 2-O-(β-D-glucopyranosyl)ascorbic acid

In addition, it is strongly suggested that 2-O-(β-D-glucopyranosyl)ascorbic acid has similar but stronger whitening effect than 2-O-(α-D-glucopyranosyl)ascorbic acid from the fact that ascorbic acid inhibits tyrosinase to suppress melanin synthesis, and pigmentation due to ultraviolet-ray irradiation is suppressed when a cream containing 2-O-(α-D-glucopyranosyl)ascorbic acid is applied to a human (Fragrance Journal, vol.25, No. March, pp.55, 1997).

Pharmacokinetics at oral ingestion of 2-O-(β-D-glucopyranosyl)ascorbic acid

In addition, when 2-O-(β-D-glucopyranosyl)ascorbic acid is orally ingested by a rat, 2-O-(β-D-glucopyranosyl)ascorbic acid which is an intact form is detected in blood, suggesting that 2-O-(β-D-glucopyranosyl)ascorbic acid is absorbed as an intact form through the intestine tract. On the other hand, as described above, when 2-O-(α-D-glucopyranosyl)ascorbic acid is orally ingested by a rat, the compound is not detected as an intact form in blood, and it is almost all degraded in the intestine tract upon absorption, and is present as ascorbic acid in blood (J.Pharmacobio-Dyn., 13, 688, 1990). That is, there is a possibility that, when orally ingested, 2-O-(α-D-glucopyranosyl)ascorbic acid is absorbed as ascorbic acid, and is rapidly degraded in blood. On the other hand, there is a high possibility that 2-O-(β-D-glucopyranosyl)ascorbic acid is also present as an intact form in blood, migrated as an intact form to tissues, and activated into ascorbic acid in tissues or cells.

From the forgoing experimental results and related findings, it is evident that 2-O-(β-D-glucopyranosyl)ascorbic acid and a composition containing it are useful as excellent provitamin C for protecting the skin and maintaining a healthy skin, can be used as a skin cosmetic or a skin protecting agent, and can be used as provitamin C which effectively migrates ascorbic acid into a body and a tissue, in foods.

A koji mold used in the present invention may be any mold as far as it is a mold belonging to the genus *Aspergillus,* and examples of such mold include a mold belonging to *Aspergillus oryzae, Aspergillus kawachii* or *Aspergillus awamori,* a strain belonging to them, as well as variants thereof. The koji mold may be a live mold or may be a dead mold, and a live mold is preferable. The koji mold may be any one as far as an enzyme contained therein is not inactivated. The koji mold may be a koji mold itself, or may be a culture containing a koji mold in which a koji mold has been nutrient-grown therein, or a koji prepared by utilizing a strong starch glycosylation by a koji mold. As such koji, koji used for brewing sake may be used. A processed koji can be used as far as an enzyme contained in the koji mold is not inactivated. A processed koji may be, for example, a dried koji mold. Drying may be spray drying, or freeze-drying. A liquid culture of a koji mold is centrifuged, the separated supernatant is freeze-dried, and water is added, and this is also a processed koji used in the present invention. Further, a processed koji may be an extract of a koji mold. An extract may be an extract of cells obtained by treating koji mold cells using the means known per se such as immersion, grinding and the like. An extract of a koji mold may be also obtained by immersing and sterilizing cells of a koji mold in ethanol, adding a 5-fold amount of MILLI Q® ultrapure water to the precipitates obtained by centrifugation, grinding and extracting this, and concentrating the extract. The aforementioned koji mold or processed koji may be a commercially available product, and examples of such product include an enzyme preparation derived from *Aspergillus oryzae* (manufactured by Amano Enzyme Inc.; trade name BIOZYME® A), and dried powders of a koji mold for rice koji manufactured by Bio'c Inc.

The composition of the present invention will be explained. The composition for external use of the present invention which is useful as cosmetics or quasi-drugs, when applied to the skin, contains 2-O-(β-D-glucopyranosyl)ascorbic acid or a salt or ester thereof which is safe to the human body (hereinafter, abbreviated as (a) ingredient in some cases) and a koji mold or a processed koji (hereinafter, abbreviated as (b)

ingredient in some cases). However, since when the (a) ingredient and the (b) ingredient are stored for a long term in the state where they are mixed, a reaction of degrading the (a) ingredient progresses in some cases, a composition containing the (a) ingredient and a composition containing the (b) ingredient are separately stored, and both compositions may be applied to the skin surface. Therefore, the present invention includes not only a composition containing both of an (a) ingredient and a (b) ingredient, but also a set or a combination of an (a) ingredient-containing composition and a (b) ingredient-containing composition. In addition, the present invention also includes use of a (b) ingredient-containing composition for promoting permeation of an (a) ingredient into the skin. A preparation of the present invention at use may be a preparation containing an (a) ingredient and a (b) ingredient, or may be a preparation obtained by blending a (b) ingredient-containing composition with an (a) ingredient or an (a) ingredient-containing composition. The preparation of the present invention, that is, a preparation containing an (a) ingredient and a (b) ingredient, or a set of an (a) ingredient-containing composition and a (b) ingredient-containing composition, or an (a) ingredient-containing composition may be usually a composition for external use, or a cosmetic, or a quasi-drug, or a medicament. Examples of the cosmetic include basic cosmetics such as lotion, milky lotion, and essence; makeup cosmetics such as foundation; hair cosmetics; cleaning cosmetics; lip cosmetics; oral cavity cosmetics; nail cosmetics; eyeliner cosmetics; bath cosmetics; and sunscreen cosmetics. Examples of the medicament or quasi-drug include medicated cosmetics, and hair restorers in addition to eye drops for dry eye.

A preferable aspect of the present invention will be explained.

A content of 2-O-(β-D-glucopyranosyl)ascorbic acid in the present composition, that is, a composition containing an (a) ingredient and a (b) ingredient, or a composition obtained by mixing a composition containing an (a) ingredient with a composition containing a (b) ingredient at use is not particularly limited, but can vary widely, and is usually 0.1 to 30% by weight, preferably 0.5 to 10% by weight, relative to a total weight of a composition. A koji mold or a processed koji in a composition cannot be said indiscriminately, but is usually about 0.2 to 100% by weight.

In the (a) ingredient-containing composition of the present invention, in addition to the (a) ingredient, ingredients such as various coloring materials, oily ingredients, fluorine compounds, resins, viscosity adjusting agents, antiseptics or sterilizers, perfumes, other humectants, salts, alcohols, antioxidants, buffers, neutralizing agents, pH adjusting agents, insect repellents and the like which are usually blended in cosmetics may be used.

As an example of coloring materials, any coloring materials may be used regardless of a shape (spherical, bar-like, needle-like, plate-like, indeterminate shape, scaly, spindle-shaped, etc.), a particle diameter (mist-like, fine particle, pigment glade, etc.), and a particle structure (porous, non-porous, etc.) as far as they are used in normal cosmetics, and examples of such coloring materials include inorganic powders, organic powders, surfactant metal salt powders, colored pigments, pearl pigments, metal powder pigments, natural pigments and the like, specifically, powders selected from, as inorganic powders, pigment grade titanium oxide, zirconium oxide, pigment grade zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, rouge mica, biotite, lithia mica, silicic acid, silicic anhydride, aluminum silicate, magnesium silicate, aluminum magnesium silicate, calcium silicate, barium silicate, strontium silicate, tungstic acid metal salt, hydroxyapatite, vermiculite, hidilite, bentonite, montmorillonite, hectorite, zeolite, ceramic powder, secondary calcium phosphate, alumina, aluminum hydroxide, boron nitride, silica, fine particle titanium oxide, fine particle zinc oxide, fine particle cerium oxide and the like; as organic powders, polyamide powder, polyester powder, polyethylene powder, polypropylene powder, polystyrene powder, polyurethane powder, benzoguanamine powder, polymethylbenzoguanamine powder, polytetrafluoroethylene powder, polymethyl methacrylate powder, cellulose, silk powder, nylon powder, 12 nylon, 6 nylon, silicone powder, silicone rubber powder, silicone elastomer spherical powder, styrene-acrylic acid copolymer, divinylbenzene/styrene copolymer, vinyl resin, urea resin, phenol resin, fluororesin, silicon resin, acryl resin, melamine resin, epoxy resin, polycarbonate resin, microcrystalline fiber powder, starch powder, laurolyllysine and the like; as surfactant metal salt powders (metal soap), zinc stearate, aluminum stearate, calcium stearate, magnesium stearate, zinc myristate, magnesium myristate, zinc cetylphosphate, calcium cetylphosphate, sodium zinc cetylphosphate and the like; as colored pigments, inorganic red pigments such as iron oxide, iron hydroxide, and iron titanate, inorganic brown pigments such as γ-iron oxide and the like, inorganic yellow pigments such as yellow iron oxide, ocher and the like, inorganic black pigments such as black iron oxide, carbon black and the like, inorganic violet pigments such as manganese violet, cobalt violet and the like, inorganic green pigments such as chromium hydroxide, chromium oxide, cobalt oxide, cobalt titanate and the like, inorganic blue pigments such as Prussian blue, ultramarine and the like, lake of tar pigment, lake of natural pigment, and synthetic resin powders obtained by compounding these powders; as pearl pigments, titanium oxide-covered mica, bismuth oxychloride, titanium oxide-covered bismuth oxychloride, titanium oxide-covered talc, scale foil, titanium oxide-covered colored mica and the like; as tar pigments, Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207 and the like; as natural pigments, carminic acid, laccaic acid, carsamine, brazilin, crosin and the like, and these powders which are compounded, or treated with general lubricants, silicone oils, fluorine compounds, surfactants or the like in such a range that the effect of the present invention is not deteriorated can also be used as described above. For example, powders may be surface-treated in advance by fluorine compound treatment, silicone resin treatment, pendant treatment, silane coupling agent treatment, titanium coupling agent treatment, lubricant treatment, N-acylated lysine treatment, polyacrylic acid treatment, metal soap treatment, amino acid treatment, inorganic compound treatment, plasma treatment, or mechanochemical treatment, and one or two or more surface treatments may be used together, if necessary. In the present invention, one or more powders of these powders can be used in combination. Examples of the oily ingredients include avocado oil, linseed oil, almond oil, insect wax, perilla oil, olive oil, cacao butter, kapok wax, kaya oil, carnauba wax, liver oil, candelilla wax, beef tallow, beef foot fat, beef bone fat, hardened tallow, apricot-kernel oil, spermaceti, hardened oil, wheat germ oil, sesame oil, rice germ oil, rice bran oil, beet wax, sasanqua oil, safflower oil, shea butter, Chinese tung oil, cinnamon oil, jojoba wax, shellac wax, turtle oil, soybean oil, tea seed oil, camellia oil, evening prime-rose oil, corn oil, lard, rape seed oil, Japanese tung oil, bran wax, germ oil, horse butter, purshic oil, palm oil, palm kernel oil, castor oil, hardened castor oil, castor oil fatty acid methyl ester, sunflower oil, grape oil, bayberry wax, jojoba oil, macadamia nut oil, beeswax, mink oil, cottonseed oil, cotton wax, Japan wax, Japan kernel wax, montan wax, coconut oil, hardened coconut oil, coconut oil fatty acid triglyceride, mutton tallow, peanut oil, lanolin, liquid lanolin, reduced lanolin, lanolin alcohol, hard lanolin, lanolin acetate, lanolin fatty acid isopropyl ester, hexyl laurate, POE lanolin alcohol ether, POE lanolin alcohol acetate, lanolin fatty acid polyethylene glycol, POE hydrogenated lanolin alcohol ether, yolk oil and the like; as a hydrocarbon oil, ozokerite, squalane, squalene, ceresin, paraffin, paraffin wax, liquid paraffin, pristane, polyisobutylene, microcrystalline wax, vaseline and the like; as a higher fatty acid, lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, 12-hydroxystearic acid and the like; as a higher alcohol, lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, phytosterol, POE cholesterol ether, monostearyl glycerin ether (batyl alcohol), monooleyl glycerin ether (selachyl alcohol) and the like; as an ester oil, diisobutyl adipate, 2-hexyldecyl adipate, di-2-heptylundecyl adipate, N-alkylglycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gumester, oleyl oleate, octyldodecyl oleate, decyl oleate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmiate, 2-hexyldecyl palmitate, 2-heptylundecyl palmitate, cholesteryl 12-hydroxystearylate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, N-lauroyl-L-glutamic acid-2-octyldodecyl ester, diisostearyl malate and the like; as a glyceride oil, acetoglyceryl, glyceryl triisooctanoate, glyceryl triisostearate, glyceryl triisopalmitate, glyceryl monostearate, glyceryl di-2-heptylundecanoate, glyceryl trimyristate, diglyceryl isostearate myristate and the like.

Examples of the antiseptic include paraoxybenzoic acid alkyl ester, benzoic acid, sodium benzoate, sorbic acid, potassium sorbate, phenoxyethanol and the like, and examples of the sterilizing agent include benzoic acid, salicylic acid, carbolic acid, sorbic acid, paraoxybenzoic acid alkyl ester, parachlorometacresol, hexachlorofen, benzalkonium chloride, chlorhexidine chloride, trichlorocarbanilide, trichlosan, photosensitive element, phenoxyethanol and the like.

In addition, examples of the humectant include polyhydric alcohols such as glycols, and polysaccharides, such as ethylene glycol, propylene glycol, butylene glycol, diethylene glycol, dipropylene glycol, glycerin, diglycerin, sorbitol, malvitol, trehalose, raffinose, xylitol, mannitol, polyethylene glycol, polyglycerin and the like. It is preferable that these are used alone, or by mixing two or more kinds, in the present invention.

Examples of the viscosity adjusting agent include plant polymers such as gum arabi, tragacanth, arabinogalactan, locust bean gum (carob gum), guar gum, karaya gum, carrageenan, pectin, agar, quince seed (marmelo), starch (rice, corn, potato, wheat), algecolloid, tranto gum, locust bean gum and the like, polymers derived from microorganisms such as xanthan gum, dextran, succinoglucan, pullulan and the like, polymers derived from animal such as collagen, casein, albumin, gelatin and the like, starch polymers such as carboxymethyl starch, methylhydroxypropyl starch and the like, cellulose polymers such as methylcellulose, ethylcellulose, methylhydroxypropylcellulose, carboxymethylcellulose, hydroxymethylcellulose, hydroxypropylcellulose, nitrocellulose, sodium cellulose sulfate, sodium carboxymethylcellulose, crystalline cellulose, and cellulose powder, alginic acid polymers such as sodium alginate, propylene glycol alginate and the like, vinyl polymers such as polyvinyl methyl ether, polyvinylpyrrolidone, carboxyvinyl polymer and the like, polyoxyethylene-based polymers such as polyethylene glycol and the like, polyoxyethylene polyoxypropylene copolymer-based polymers, acryl-based polymers such as sodium polyacrylate, polyethyl acrylate, polyacrylic acid amide and the like, polyethyleneimine, cation polymer, and inorganic thickners such as bentonite, aluminum magnesium silicate, laponite, smectite, saponite, hectrite, silicic acid anhydride and the like. In addition, as other thickners, there is an oil-soluble gelling agent, and examples include metal soaps such as aluminum stearate, magnesium stearate, zinc myristate and the like, amino acid derivatives such as N-lauroyl-L-glutamic acid, α,γ-di-n-butylamine and the like, dextrin fatty acid esters such as dextrin palmitic acid ester, dextrin stearic acid ester, dextrin 2-ethylhexanoic acid palmitic acid ester and the like, sucrose fatty acid esters such as sucrose palmitic acid ester, sucrose stearic acid ester and the like, benzylidene derivatives of sorbitol such as monobenzylidene sorbitol, dibenzylidene sorbitol and the like, and organic-modified clay minerals such as dimethylbenzyldodecylammonium montmorillonite clay, dimethyldioctadecylammonium montmorillonite, octadecyldimethylbenzylammonium montmorillonite and the like.

This (a) ingredient-containing composition can be used not only alone as a composition for external use, but also as a mixture with the aforementioned ingredients, it can be used as medicated cosmetics such as lotions, milky lotions, creams, packs, soaps and the like as cosmetics or quasi-drugs, or as skin external agents such as lotions, milky lotions, creams, ointments and the like as medicaments.

The (b) ingredient-containing composition may be only a koji mold or a processed koji, or may be diluted with a liquid diluent such as water, alcohol and the like, or a solid diluent such as paraffin and the like, or a semi-solid diluent such as liquid paraffin and the like. Alternatively, in the aforementioned (a) ingredient-containing composition, a composition using a (b) ingredient in place of an (a) ingredient may be used as a (b) ingredient-containing composition.

The composition containing an (a) ingredient and a (b) ingredient is prepared by mixing an (a) ingredient, a (b) ingredient and various ingredients explained in the aforementioned (a) ingredient-containing composition, or may be a composition obtained by mixing the (a) ingredient-containing composition and the (b) ingredient-containing composition.

When applied to the skin surface as a skin external agent, an (a) ingredient-containing composition and a (b) ingredient-containing composition are mixed. After mixing, the mixture is applied to the skin surface. Upon mixing both compositions, the ratio of an (a) ingredient and a (b) ingredient to be used is about 1:0.001 to 0.1, preferably about 1:0.005 to 0.05 as expressed by a weight ratio.

Mixing of an (a) ingredient-containing composition and a (b) ingredient-containing composition may be performed by the well-known method.

A preferable aspect when the composition of the present invention is a cosmetic will be explained. When the cosmetic is a lotion, the lotion is obtained by dissolving or dispersing an (a) ingredient-containing composition and a (b) ingredient-containing composition in a solvent.

When the cosmetic is a milky lotion, the milky lotion is obtained by blending an (a) ingredient-containing composition and a (b) ingredient-containing composition in a mixed solution obtained by emulsifying raw materials except for the (a) ingredient and the (b) ingredient, for example, using a homogenizer or the like.

The thus prepared composition of the present invention at use is used in basic cosmetics such as lotions, milky lotions, and essence, makeup cosmetics such as foundations, hair cosmetics, cleaning cosmetics, lip cosmetics, oral cavity cosmetics, nail cosmetics, eyeliner cosmetics, bath cosmetics, and sunburn/sunscreen cosmetics. The composition is also used in medicaments or quasi-drugs, and examples of them include medicated cosmetics, and hair restorers in addition to eye drops for dry eye.

EXAMPLES

The present invention will be explained more specifically below by way of Examples, but it goes without saying that the scope of the present invention is not limited to these Examples.

Example 1

Synthesis of 2-O-(2,3,4,6-tetra-O-acetyl-(β-D-glucopyranosyl)ascorbic acid:

5,6-O-isopropylidene ascorbic acid (2 g, 9.3 mmol) was dissolved in DMSO (20 ml), and to the solution were added potassium carbonate (1.3 g, 9.4 mmol) and benzyl bromide (1.1 ml, 9.3 mmol), and the mixture was stirred at 50° C. for 4 hours. Water was added to the reaction solution, and the solution was made acidic with 1N-HCl, extracted with ethyl acetate, washed successively with water and an aqueous saturated sodium chloride solution, dried over anhydrous $MgSO_4$, concentrated under reduced pressure, and purified by silica gel chromatography (AcOEt/n-Hexane=3:1) to obtain 1.1 g of 3-O-benzyl-5,6-O-isopropylidene ascorbic acid (yield: 39%).

A mixture of this benzyl derivative (0.6 g, 2.0 mmol) and 2,3,4,6-tetra-O-acetyl-1-O-(2,2,2-trichloroethoxycarbonyl)-β-D-glucopyranose (2.1 g, 4.0 mmol) was heated to melt at 120 to 130° C. Three hours after the reaction, the reaction solution was purified by column chromatography (gradient from 25% to 50% AcOEt/n-Hexane) to obtain 850 mg of 2-O-(2,3,4,6-tetra-O-acetyl-(β-D-glucopyranosyl)-3-O-benzyl-5,6-O-isopropylidene ascorbic acid (yield: 67%).

The glycoside (850 mg, 1.3 mmol) was dissolved in ethyl acetate (40 ml), 10% Pd-C (200 mg) was added thereto, and hydrogenolysis was carried out. After two hours, the catalyst was removed by filtration, and the filtrate was concentrated to obtain about 750 mg of 2-O-(2,3,4,6-tetra-O-acetyl-(β-D-glucopyranosyl)-5,6-O-isopropylidene ascorbic acid.

The debenzylated derivative (500 mg, 0.9 mmol) was dissolved in acetic acid (5 ml), and water (5 ml) was added. The solution was heated to stir at 50 to 60° C. for 1.5 hours. The reaction solution was concentrated, and the residue was washed successively with water and an aqueous saturated sodium chloride solution, dried over anhydrous $MgSO_4$, and concentrated under reduced pressure. The resulting residue was crystallized from ethyl acetate-hexane to obtain 320 mg of 2-O-(2,3,4,6-tetra-O-acetyl-β-D-glucopyranosyl)ascorbic acid (yield: 48%). PMR (δ ppm, DMSO-$d_6$); 1.94-2.01(12H), 3.42(3H, m), 3.7-4.3(4H, m), 4.7-5.1 (4H, m), 5.3-5.4(2H, m), 12.00(1H, br). FABMS(+) m/z: 507.

Example 2

Synthesis of 2-O-(β-D-glucopyranosyl)ascorbic acid:

2-O-(2,3,4,6-tetra-O-acetyl-β-D-glucopyranosyl)ascorbic acid (300 mg, 0.6 mmol) was dissolved in methanol (10 ml), and to the solution was added a solution in which potassium carbonate (600 mg) had been dissolved in water (9 ml). The mixture was stirred for 30 minutes. The reaction solution was neutralized with AMBERLITE® IR-120 ($H^+$), and filtered to remove the resin. The filtrate was washed successively with methanol and 50% aqueous methanol solution. The filtrate and the washing solution were combined, and concentrated, and then water was added thereto, followed by freeze-drying to obtain 2-O-β-D-glucopyranosyl)ascorbic acid as amorphous crystals (190 mg, yield: 100%). PMR (δ ppm, $D_2O$); 3.1-3.3 (4H, m), 3.4-3.5 (3H, m), 3.58(1H d) , 3.80(1H, t), 4.61(1H, d), 4.66(1H, d). FABMS(−) m/z: 337.

Example 3

Measurement of content of 2-O-(β-D-glucopyranosyl) ascorbic acid in Chinese wolfberry Using, as an index, a retention time 2.63 minutes in high performance liquid chromatography (LC-10Ai system manufactured by Shimadzu Corporation, column: INERTSIL® ODS-3 (manufactured by GL Science, 4.6×150 mm, 5 µm), mobile phase: 20% MeOH/20 mM phosphoric acid/5 mM tetra-n-amylammonium bromide, flow rate: 1.0 mL/min, column temperature: 35° C., detection wavelength: 254 nm) of a chemically synthesized product of 2-O-(β-D-glucopyranosyl)ascorbic acid, an extract obtained by immersing 3 g of a dried plant in a 10-fold amount of 70% ethanol at room temperature for 7 days was diluted 10-fold with 1.5% metaphosphoric acid/5M KOH (pH 3.5), and the diluted solution was used as a test sample to search naturally occurring 2-O-β-D-glucopyranosyl)ascorbic acid. As a result, the presence of a peak corresponding to 2-O-β-D-glucopyranosyl)ascorbic acid was confirmed in an extract of Lycium chinense produced in Neika and Kahoku. In addition, the presence of such compound was similarly recognized in a sample obtained by adding a 2-fold amount of 70% ethanol to 100 g of a raw fruit of Chinese wolfberry produced in Neika, and treating the mixture similarly. On the other hand, an extracted solid was obtained by concentrating a part (5 mL) of the above extract under reduced pressure, and measuring a weight after freeze-drying. Taking a calibration line using an extracted solid and a chemically synthesized product, a concentration in an extract, and a dilution ratio into consideration, a content per extract was 0.86 to 1.2%.

Example 4

Purification of 2-O-(β-D-glucopyranosyl)ascorbic acid contained in Lycium chinense One hundred gram of Lycium chinense produced in Neika was crushed with a tablet grinder TS-10M type manufactured by Tosho Corporation, and 800 mL of 30% ethanol was added thereto. The material was immersed at room temperature for 6 days, and then filtered. The filtrate was concentrated under reduced pressure, and freeze-dried to obtain 65.7 g. Apart (1.94 g) of this extract (content of 2-O-(β-D-glucopyranosyl) ascorbic acid; 0.86%) was dissolved in distilled water to a volume of 40 mL (pH 4.5, electrical conductivity 1.7 mS/cm). This sample was passed through DOWEX® 1-X8 column (acetate form, 1.5×12 cm) at SV=1. After passage, washing with an about 10 column volume (200 mL) of distilled water, and elution with 0 to 0.1 M acetic acid linear gradient concentration (100 mL×2), 0.1 to 1.0 M acetic acid linear gradient concentration (100 mL×2), and 1.0 M acetic acid were performed. An absorbance at 280 nm was measured, and elution of 2-O-(β-D-glucopyranosyl) ascorbic acid was studied by high performance liquid chromatography using a retention time of a chemically synthesized product as a control. An apparatus, and a column temperature were the same as those of Example 1, but other condition was changed to column: INERTSIL® ODS-3 (manufactured by GL Science, 3.0×150 mm, 5 µm), flow rate: 0.3 mL/min, detection wavelength: 245 nm, mobile phase: 2% MeOH -0.2 M $KH_2PO_4$/$H_3PO_4$ (pH 3.0)—0.2 mM EDTA—0.5 mM dodecyltrimethylammonium chloride, and a retention time of a chemically synthesized product 2-O-(β-D-glucopyranosyl) ascorbic acid was found to be 6.5 minutes. As a result of study by high performance liquid chromatography, the substance absorbed onto a column was eluted in fractions 19 to 25 of 0.1 to 1.0 M acetic acid linear gradient concentration (26 mg, total recovery rate of fractions 19 to 25; 78%, purity 50%).

Example 5

Enzymatic synthesis of 2-O-(β-D-glucopyranosyl)ascorbic acid

Using, as an index, a retention time of 5.2 minutes in LC system manufactured by GILSON (master pump 305 type, UV detector 116 type), column: INERTSIL® ODS-3 (manufactured by GL Science, 4.6×150 mm, 5 µm), mobile phase: 20% MeOH-20 mM phosphoric acid-5 mM tetra-n-amylammonium bromide, flow rate: 0.5 ml/min, detection wavelength: 254 nm) of a chemically synthesized product of 2-O-(β-D-glucopyranosyl)ascorbic acid, commercially available cellulase, (β-glucosidase, and β-glucanase enzyme preparations were searched. An enzyme reaction system was obtained by being dissolved in a 10 mM acetate buffer (pH 5.0) to 1 ml so that cellobiose became to be 0.3 M and ascorbic acid became to be 0.2 M. After addition of 50 µl of an enzyme solution, the reaction was initiated at 37° C. The reaction was stopped by heating at 100° C. for 5 minutes, and β-D-glucopyranosylascorbic acid produced was analyzed by high performance liquid chromatography. As a result, it was found that cellulase (manufactured by Sigma), β-glucosidase (Toyobo Co., Ltd., Nakarai Tesque), CELLULOSIN T2 (Hankyu Kyoei Bussan), cellulase "ONOZUKA" RS, "ONOZUKA" FA and PANCELLASE BR (Yakult Pharmaceutical Ind. Co., Ltd.) have (β-glucosyltransferase activity. Free ascorbic acid appeared a position of 4.0 minutes, while peaks were recognized at positions of 3.6 minutes and 5.2 minutes before and after that position, and they were designated as substance X and substance Y. A conversion rate of the substance X indicated 15.7%, and a conversion rate of the substance Y indicated 0.8%. By cochromatography analysis of this substance X and substance Y with chemically synthesized products, a retention time of the substance X was consistent with that of 6-O-(β-D-glucopyranosyl)ascorbic acid, and a retention time of the substance Y was consistent with that of 2-O-(β-D-glucopyranosyl)ascorbic acid.

Further, after removal of the coexisting protein was removed with a 10,000 molecular weigh cut-off UF membrane, substances were fractionated using high performance liquid chromatography {LC system manufactured by GILSON (master pump 305 type, UV detector 116 type), column: SHODEX® SUGAR SH1011 (manufactured by SHOWA DENKO K.K.), mobile phase: 0.1 M acetic acid, flow rate: 0.5 mL/min, column temperature: 30° C., detection: differential refractometer, 0.25 ml fraction} in order to remove free ascorbic acid. A fraction containing a substance X and a substance Y was eluted at 29 to 31 fractions, and 24.7 µg of an authentic product in a yield of 96%.

Further, the product was subjected to high performance liquid chromatography to obtain a highly purified product. Under the condition of LC system manufactured by GILSON (master pump 305 type, UV detector 116 type), column: DEVELOSIL® ODS-UG-5 (manufactured by Nomura Chemical Co., Ltd., 4.6×250 mm, 5 µm), mobile phase: 5% methanol—20 mM ammonium formate—5 mM di-n-butylamine acetate, flow rate: 0.5 mL/min, and detection wavelength: 254 nm, fractions were obtained using a fraction collector FC-203B type (manufactured by GILSON) every 0.5 minute. Fractions corresponding to a substance X and a substance Y were concentrated under reduced pressure, freeze-dried, dissolved in heavy water, and nuclear magnetic resonance spectrum was measured to compare with a chemically synthesized product 2-O-(β-D-glucopyranosyl)ascorbic acid. In HSQC spectrum, chemical shifts of the carbon atoms at positions of 4, 5, and 6 in the partial structure of a chemically synthesized ascorbic acid were 73, 73 and 66 ppm, respectively, while in the substance X, all chemical shifts of the carbon atoms at positions of 4, 5, and 6 were 73 ppm, and only a carbon corresponding to the position 6 was shifted to down magnetic field, therefore, the substance X is determined to be 6-O-(β-D-glucopyranosyl)ascorbic acid.

Since the substance Y was consistent with a chemically synthesized product 2-O-(β-D-glucopyranosyl)ascorbic acid in one-dimensional PMR spectrum comparison, it is determined to be 2-O-(β-D-glucopyranosyl)ascorbic acid.

Example 6

Purification of ((3-D-glucopyranosyl)ascorbic acid

Twenty milligram of a cellulase preparation (Sigma) was dissolved in 1 ml of 20 mM acetate buffer (pH 5.0), and the solution was subjected to DOWEX® MARATHON WBA (resin 0.5 ml, manufactured by Dow Chemical) equilibrated with the same buffer to obtain a void fraction. This enzyme solution was added to 10 ml of 20 mM acetate buffer (pH 5.0) in which 0.35 g of ascorbic acid and 1 g of cellobiose were dissolved. The reaction at 37° C. for 2 days afforded a reaction solution of 11.8% of 6-O-(β-D-glucopyranosyl)ascorbic acid and 0.8% of 2-O-(β-D-glucopyranosyl)ascorbic acid. The solution was filtered with an UF membrane to recover and remove the enzyme, thereby to obtain a solution (pH 4.3, electrical conductivity 1.6 mS/cm). The solution was charged on a column of DOWEX® 1-X8 (acetate form, 1.5×12 cm) at SV=2.5. After the charge, washing with an about 10 column volume (200 mL) of distilled water, and elution with 0 to 0.1 M acetic acid linear gradient concentration (80 mL×2), and 0.1 to 1.0 M acetic acid linear gradient concentration (80 mL×2) were performed. A 6-O-(β-D-glucopyranosyl)ascorbic acid-enriched fraction (fractions 65 to 68), an unreacted ascorbic acid-enriched fraction, and a 2-O-(β-D-glucopyranosyl)ascorbic acid-enriched fraction (fractions 101 to 108) were fractionated in this order. The fractions 101 to 108 were collected as a 2-O-(β-D-glucopyranosyl)ascorbic acid-enriched fraction (2.4 mg, recovery rate 45%).

Example 7

Protective effect of 2-O-(β-D-glucopyranosyl)ascorbic acid on cell death of keratinocytes (HaCaT) derived from human skin epidermis by ultraviolet-ray B wave (UVB) irradiation:

Human skin keratinocytes HaCaT (cell line gifted by Dr. Fusenig of Heidelberg University) was seeded to 10% bovine fetal serum (FBS)-containing Dulbecco modified Eagle medium (DMEM) at 10,000 cells/well in a 24-well plate, and after 18 hours, 35 millijoule/square centimeter ($mJ/cm^2$) of UBV (maximum wavelength 312 nm) was irradiated. Two hours before the irradiation, 20 to 100 μM of 2-O-(β-D-glucopyranosyl)ascorbic acid was added, and such ascorbic acid was removed immediately before the irradiation and then rinsed. Irradiation was performed in PBS in the absence of a drug, and after irradiation, culturing was continued in a FBS 10%-containing DMEM medium, and 24 hours after irradiation, a cell survival rate was investigated by a method for measuring mitochondrion dehydrogenase activity with the use of 2-(4-iodophenyl)-3-(4-nitrophenyl)-5-(2,4-disulfophenyl)-2H-tetrazolium monosodium salt (WST-1). The results are shown in FIG. 1. Similarly, as Comparative Example, 2-O-(α-D-glucopyranosyl) ascorbic acid and ascorbic acid were studied, and the results are also shown in FIG. 1.

Example 8

Figure 2:
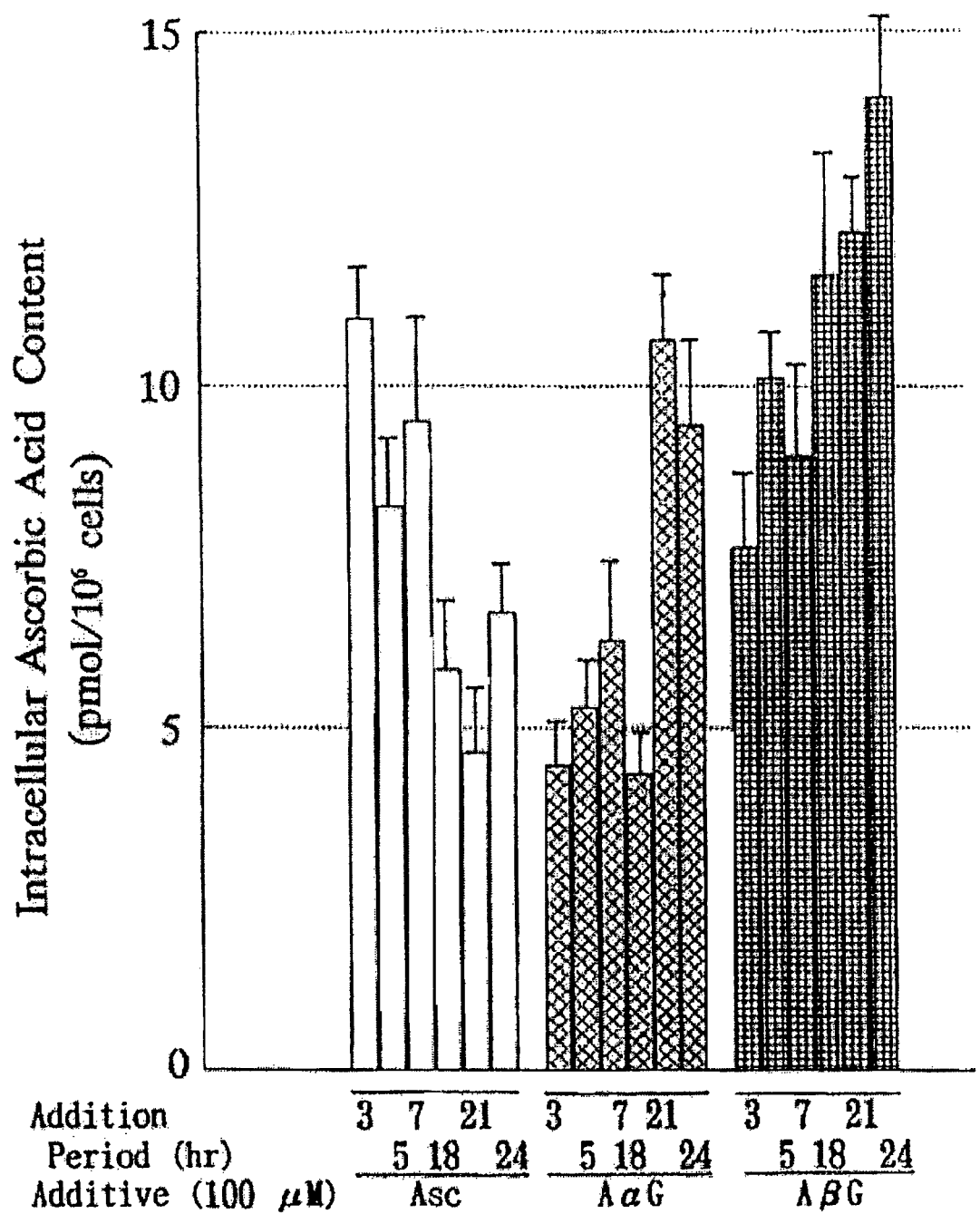
FIG. 2 shows an effect of 2-O-(β-D-glucopyranosyl)ascorbic acid on an intracellular ascorbic acid concentration in human skin keratinocytes.

Effect of 2-O-(β-D-glucopyranosyl)ascorbic acid on concentration of intracellular ascorbic acid in human skin keratinocytes:

Human skin keratinocytes HaCaT are seeded in a dish having a diameter of 100 millimeter at 370,000 cells. Sixteen hours after culturing, 100 μM of 2-O-(β-D-glucopyranosyl) ascorbic acid dissolved in a 10% FBS-containing DMEM medium supplemented with 40% HaCaT 24 hours serum-free cultured solution is added thereto. At 3 to 24 hours after addition, a medium is removed, rinsed twice with ice-cooled PBS, and a cell sheet is peeled with trypsin to make single cell state. This is suspended in PBS containing 50 μM dithiothreitol (DTT), and rinsed three times by centrifugation. The cell suspension is disrupted with a potter-type teflon (registered trademark) homogenizer, and then frozen and thawed twice. The supernatant is analyzed with MOLECUT (manufactured by Nippon Millipore, pressure ultrafiltration unit, fractionation molecular weight 10,000, polyethersulfone membrane), and an amount of intracellular ascorbic acid is analyzed with a coulometric electrochemical detector (ESA Co, Bedford, Mass., 200 mV) by high performance liquid chromatography (AS-8020 system manufactured by Tosoh Corporation, column: SHODEX® ODSpak (manufactured by SHOWA DENKO K.K., 4.6×150 mm), mobile phase: 0.1 M $KH_2PO_4$-$H_3PO_4$ (pH 2.35)-0.1 mM EDTA-2Na, flow rate: 1.5 mL/min). The results are shown in FIG. 2. Similarly, as Comparative Example, 2-O-(α-D-glucopyranosyl)ascorbic acid, and ascorbic acid are studied, and the results are also shown in FIG. 2.

Example 9

Figure 3:
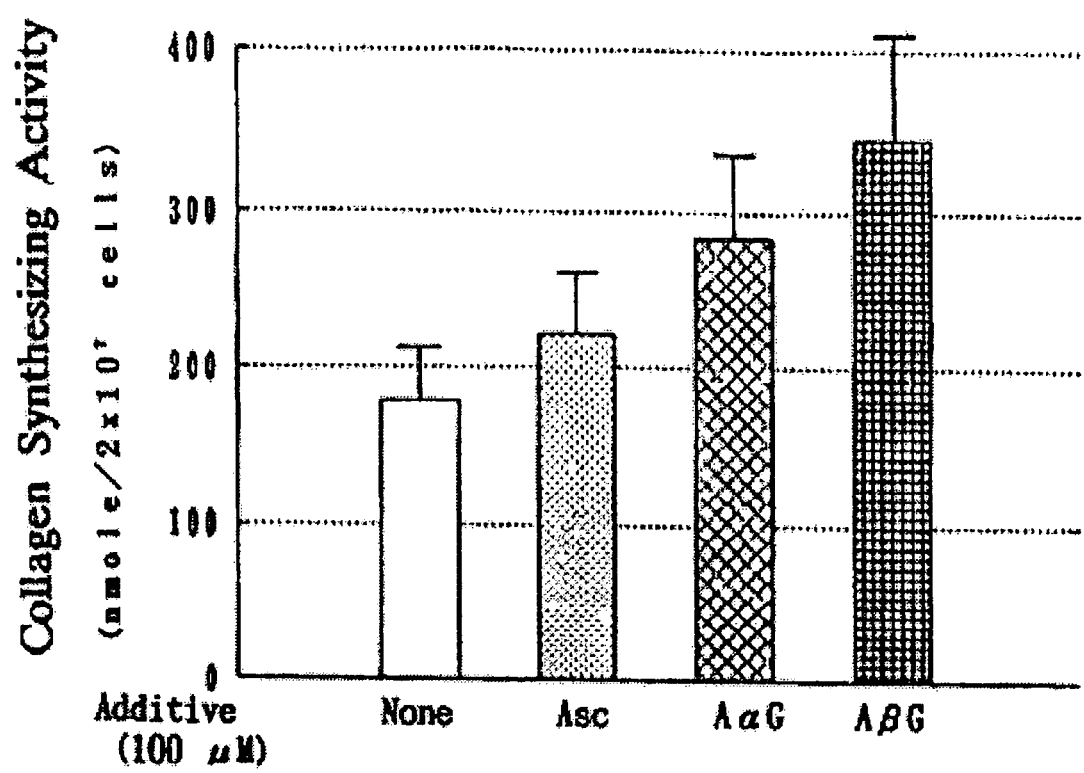
FIG. 3 shows a protective effect of 2-O-(β-D-glucopyranosyl)ascorbic acid on collagen synthesis of fibroblasts (NHDF) derived from the human skin dermis.

Promotion effect of 2-O-(β-D-glucopyranosyl)ascorbic acid on collagen synthesis of normal human dermal fibroblasts (NHDF):

Normal human dermal fibroblasts NHDF are seeded in a dish having a diameter of 100 millimeter at 370,000 cells. After 16 hours, 100 μM of 2-O-(β-D-glucopyranosyl)ascorbic acid is added to a 10% FBS-containing DMEM medium supplemented with 40% NHDF 24 hours serum-free cultured solution. After additional 1 hour, 0.12 mL (120 μCi) of L-(2, 3-$^3$H) proline is added, followed by culturing for 48 hours. After culturing, the medium is removed, and a cell sheet is rinsed with PBS four times. Then, cells are peeled with trypsin, cells are lysed with an alkali, and neutralized to obtain an intracellular protein. The protein is subjected to collagen degradation with collagenase of Clostridium to obtain a protein fraction, and radioactivity of the fraction is measured with a liquid scintillation counter using SCINTISOL EX-H. Separately, radioactivity of an intracellular protein fraction which has not been treated with collagenase is similarly measured with a liquid scintillation counter. A difference between respective radioactivities obtained is adopted as collagen synthesis activity. The results are shown in FIG. 3. Similarly, as Comparative Example, 2-O-(α-D-glucopyranosyl)ascorbic acid, and ascorbic acid are studied, and the results are also shown in FIG. 3.

Example 10

A human isolated skin piece (skin under earlobe of 51 years old female) for which informed consent had been obtained was divided into strip-type small pieces in a vertical direction, and this small piece was mounted in a modified Bronof diffusion cell chamber. An underside of a skin was immersed in a DMEM medium (2 mL) while supplying a nutrient, and 5% $CO_2$ was bubbled on a corneum side to maintain a pH of a medium at 7.25. An about 5 mm square double gauze impregnated with 1 mL of 100 mM 2-O-(β-D-glucopyranosyl)ascorbic acid (hereinafter, also abbreviated as AβG) {3.38% w/w, PBS (−) solution (phosphate buffered saline not containing metal salts of calcium chloride and magnesium chloride)} was touched on a corneum, and at the same time, a 25 w/w % PBS (−) solution of an enzyme preparation (manufactured by Amano Enzyme Inc., trade name BIOZYME® A) derived from *Aspergillus oryzae* was subjected to filtration and sterilization, and 1/200 (5 μL), 1/500 (2 μL) and 1/1000 (1 μL) of the solution per small piece were added to a gauze (hereinafter, also abbreviated as Bz).

Alternatively, in the aforementioned method, a suspension in which 5 mL MILLI Q® ultrapure water had been added to 1 g of a koji dry powder for rice koji manufactured by Bio'c Inc. was subjected to freezing and thawing, and disruption with a potter-type teflon (registered trademark) homogenizer, the supernatant obtained by centrifugation was filtration-sterilized, and 1/20 (50 μL), and 1/50 (20 μL) of the solution in place of Bz were added to a gauze (hereinafter, also abbreviated as Kj). In addition, in the aforementioned method, only AβG was administered without using Bz or Kj additives.

Five hours after administration, a skin small piece was excised from a modified Bronof diffusion cell, and a 10-fold amount of 0.1% trypsin PBS (−) solution was added thereto. The mixture was treated at 37° C. for 3 hours, and stirred gently to separate into the epidermis and dermis. Under no bubbling, freezing and thawing with a potter-type teflon (registered trademark) homogenizer and liquid nitrogen were performed on each of them, thereby to disrupt cells. The supernatant obtained by centrifugation of the disrupted solution was ultrafiltered, and according to a similar manner to Example 8, AβG was measured by a UV method, and amounts of total vitamin C (sum of reduced form and oxidized form) and reduced form of vitamin C were measured by an electrochemical detecting method. Thereupon, a ratio occupied in a total vitamin C amount was measured. The total amounts of vitamin C in the epidermis and dermis five hours after administration of AβG alone or coadministration with an additive are shown in Table 1. Ratios of reduced form of vitamin C occupied in the total amount of vitamin C in the epidermis and dermis five hours after administration of AβG alone or coadministration with an additive to a human isolated skin piece are shown in Table 2. Uptake amounts of AβG into the epidermis and dermis five hours after administration of AβG alone, or coadministration with an additive to a human isolated skin piece are shown in Table 3.

TABLE 1

| AβG administration amount | Administration Enzyme | Administration amount | Total vitamin C in skin (nmol/g tissue) | |
|---|---|---|---|---|
| | | | Epidermis | Dermis |
| 100 mM | None | None | 15 | 3 |
| 100 mM | Bz | 1/200 | 162 | 11 |
| | | 1/500 | 57 | 7 |
| 100 mM | Kj | 1/20 | 15 | 6 |
| | | 1/50 | 18 | 8 |

TABLE 2

| AβG administration amount | Administration Enzyme | Administration amount | Ratio (%) of reduced form of vitamin C occupied in total vitamin C in skin | |
|---|---|---|---|---|
| | | | Epidermis | Dermis |
| 100 mM | None | None | 67 | 25 |
| 100 mM | Bz | 1/200 | 82 | 60 |
| | | 1/500 | 77 | 42 |
| 100 mM | Kj | 1/20 | 77 | 40 |
| | | 1/50 | 77 | 37 |

TABLE 3

| AβG administration amount | Administration Enzyme | Administration amount | Uptake amount of AβG into skin piece | |
|---|---|---|---|---|
| | | | Epidermis | Dermis |
| 100 mM | None | None | 3,400 | 500 |
| 100 mM | Bz | 1/200 | 8,600 | 250 |
| | | 1/500 | 6,700 | 250 |
| | | 1/1000 | 3,200 | 1,300 |
| 100 mM | Kj | 1/20 | 2,300 | 960 |
| | | 1/50 | 2,600 | 1,600 |

As shown in Table 1 and Table 2, by simultaneous addition of Bz or Kj, vitamin C enrichment was also attained in the dermis which is 0.1 to 1.3 mm deep from the skin surface, where supply of vitamin C is particularly difficult, in a skin tissue. This primary effect of vitamin C enrichment leads to secondary effect of wrinkle defending effect via collagen synthesis promotion in dermis fibroblasts. In addition, as shown in Table 3, simultaneous addition of Bz or Kj, permeability of AβG which is provitamin C, from a skin surface to a deep part, was increased.

From the above results, it is seen that 2-O-(β-D-glucopyranosyl)ascorbic acid of the present invention is remarkably improved in skin permeability, and is converted into vitamin C better, due to the presence of a koji mold or a processed koji.

INDUSTRIAL APPLICABILITY

According to the present invention, a skin external composition containing an ascorbic acid derivative which is excellent in stability, persistently utilized in the living body, and is strong in antioxidant activity, and has little skin irritation, and having excellent skin permeability can be provided.

The invention claimed is:

1. A composition for external use, comprising isolated 2-O-(β-D-glucopyranosyl)ascorbic acid represented by the formula (I):

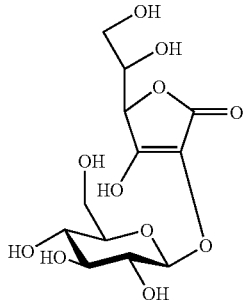

or a salt or ester thereof which is safe to the human body, and a koji mold or a processed koji.

2. The composition according to claim 1, which is a cosmetic or a quasi-drug.

3. The composition according to claim 1, wherein the 2-O-(β-D-glucopyranosyl)ascorbic acid represented by the formula (I) as defined in claim 1 is 2-O-(β-D-glucopyranosyl) ascorbic acid isolated from a plant.

4. The composition according to claim 3, wherein the plant is a plant of Solanaceae.

5. The composition according to claim 3, wherein the plant is Chinese wolfberry, or its raw fruit or its dry fruit.

6. The composition according to claim 1, wherein the koji mold or processed koji is a mold belonging to the genus *Aspergillus*.

7. The composition according to claim 1, wherein the koji mold or processed koji is a mold belonging to *Aspergillus oryzae*, *Aspergillus kawachii* or *Aspergillus awamori*.

8. A kit comprising (a) a composition comprising isolated 2-O-(β-D-glucopyranosyl)ascorbic acid represented by the formula (I) as defined in claim 1, or a salt or ester thereof which is safe to the human body, and (b) a composition comprising a koji mold or a processed koji.

9. A method for potentiating skin permeability of 2-O-(β-D-glucopyranosyl)ascorbic acid, or a salt or ester thereof which is safe to the human body, by applying the composition according to claim 1 to a skin.

* * * * *